United States Patent
Choi et al.

(10) Patent No.: US 9,359,276 B2
(45) Date of Patent: *Jun. 7, 2016

(54) MONOMER FOR HARDMASK COMPOSITION, HARDMASK COMPOSITION INCLUDING MONOMER, AND PATTERN FORMING METHOD USING HARDMASK COMPOSITION

(71) Applicants: Yoo-Jeong Choi, Uiwang-si (KR);
Hyo-Young Kwon, Uiwang-si (KR);
Youn-Jin Cho, Uiwang-si (KR);
Yun-Jun Kim, Uiwang-si (KR);
Young-Min Kim, Uiwang-si (KR);
Yong-Woon Yoon, Uiwang-si (KR);
Chung-Heon Lee, Uiwang-si (KR)

(72) Inventors: Yoo-Jeong Choi, Uiwang-si (KR);
Hyo-Young Kwon, Uiwang-si (KR);
Youn-Jin Cho, Uiwang-si (KR);
Yun-Jun Kim, Uiwang-si (KR);
Young-Min Kim, Uiwang-si (KR);
Yong-Woon Yoon, Uiwang-si (KR);
Chung-Heon Lee, Uiwang-si (KR)

(73) Assignee: CHEIL INDUSTRIES, INC., Gumi-si, Gyeongsangbuk-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/365,751

(22) PCT Filed: Nov. 21, 2012

(86) PCT No.: PCT/KR2012/009870
§ 371 (c)(1),
(2) Date: Jun. 16, 2014

(87) PCT Pub. No.: WO2013/100365
PCT Pub. Date: Jul. 4, 2012

(65) Prior Publication Data
US 2015/0008212 A1    Jan. 8, 2015

(30) Foreign Application Priority Data

Dec. 30, 2011 (KR) .................. 10-2011-0147381

(51) Int. Cl.
*C07C 39/14* (2006.01)
*C07C 39/12* (2006.01)
*G03F 7/11* (2006.01)
*G03F 7/09* (2006.01)
*G03F 7/004* (2006.01)
*G03F 7/075* (2006.01)
*G03F 7/30* (2006.01)
*G03F 7/36* (2006.01)
*B05D 1/00* (2006.01)
*B05D 3/00* (2006.01)
*B05D 3/02* (2006.01)
*B05D 3/06* (2006.01)
*C09D 173/00* (2006.01)

(52) U.S. Cl.
CPC .............. *C07C 39/14* (2013.01); *B05D 1/005* (2013.01); *B05D 3/007* (2013.01); *B05D 3/0254* (2013.01); *B05D 3/06* (2013.01); *C07C 39/12* (2013.01); *C09D 173/00* (2013.01); *G03F 7/004* (2013.01); *G03F 7/0752* (2013.01); *G03F 7/094* (2013.01); *G03F 7/11* (2013.01); *G03F 7/30* (2013.01); *G03F 7/36* (2013.01); *C07C 2103/50* (2013.01); *C07C 2103/54* (2013.01)

(58) Field of Classification Search
None
See application file for complete search history.

(56) References Cited

U.S. PATENT DOCUMENTS

| 8,952,373 B2* | 2/2015 | Choi et al. ................ 257/40 |
| 2004/0110093 A1 | 6/2004 | Afzali-Ardakani |
| 2010/0021830 A1 | 1/2010 | Kim et al. |
| 2011/0151376 A1 | 6/2011 | Rahman et al. |
| 2011/0155944 A1 | 6/2011 | Cho et al. |

FOREIGN PATENT DOCUMENTS

| CN | 101470352 A | 7/2009 |
| KR | 10-2007-0002595 A | 1/2007 |
| KR | 10-2008-0107210 A | 12/2008 |
| KR | 10-2009-0068444 A | 6/2009 |
| KR | 10-2011-0053136 A | 5/2011 |
| TW | 2012-29672 A1 | 7/2012 |
| WO | WO-2004/007192 A1 | 1/2004 |

OTHER PUBLICATIONS

Search Report mailed May 26, 2014 in corresponding Taiwanese Patent Application No. 101150565.
International Search Report mailed Mar. 28, 2013 for PCT/KR/2012/009870.

* cited by examiner

Primary Examiner — Sin Lee
(74) Attorney, Agent, or Firm — Lee & Morse, P.C.

(57) ABSTRACT

Disclosed are a monomer for a hardmask composition represented by the Chemical Formula 1, a hardmask composition including the monomer, and a method of forming a pattern.

10 Claims, No Drawings

MONOMER FOR HARDMASK COMPOSITION, HARDMASK COMPOSITION INCLUDING MONOMER, AND PATTERN FORMING METHOD USING HARDMASK COMPOSITION

TECHNICAL FIELD

A monomer for a hardmask composition, a hardmask composition including the monomer, and a method of forming a pattern using the hardmask composition are disclosed.

BACKGROUND ART

Recently, the semiconductor industry has developed to an ultra-fine technique having a pattern of several to several tens nanometer size. Such ultra-fine technique essentially needs effective lithographic techniques.

The typical lithographic technique includes providing a material layer on a semiconductor substrate; coating a photoresist layer thereon; exposing and developing the same to provide a photoresist pattern; and etching the material layer using the photoresist pattern as a mask.

Nowadays, according to small-sizing the pattern to be formed, it is difficult to provide a fine pattern having an excellent profile by only above-mentioned typical lithographic technique.

Accordingly, a layer, called a hardmask layer, may be formed between the material layer and the photoresist layer to provide a fine pattern. The hardmask layer plays a role of an intermediate layer for transferring the fine pattern of photoresist to the material layer through the selective etching process. Accordingly, the hardmask layer requires to have characteristics such as chemical resistance, heat resistance, and etch resistance or the like to be tolerated during the multiple etching process.

On the other hand, it has been recently suggested to form a hardmask layer by a spin-on coating method instead of the chemical vapor deposition. The spin-on coating method may use the hardmask composition having dissolubility for a solvent.

However, the dissolubility and the characteristics required for the hardmask layer have the relationship against to each other, so a hardmask composition satisfying both is needed.

In addition, according to widening the application range of hardmask layer, the hardmask layer may be formed on a predetermined pattern by the spin-on coating method. In this case, the gap-fill characteristics of filling the hardmask composition in gap between patterns and the planarization characteristics are also required.

DESCRIPTION

Technical Objection

One embodiment provides a monomer for a hardmask composition that satisfies chemical resistance, heat resistance and etch resistance while ensures dissolubility for a solvent, gap-fill characteristics, and planarization characteristics.

Another embodiment provides a hardmask composition including the monomer.

Yet another embodiment provides a method of forming a pattern using the hardmask composition.

Technical Solution

According to one embodiment, a monomer for a hardmask composition represented by the following Chemical Formula 1 is provided.

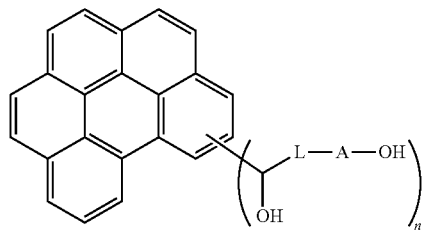

[Chemical Formula 1]

In Chemical Formula 1,

A is a substituted or unsubstituted C6 to C30 arylene group,

L is a single bond or a substituted or unsubstituted C1 to C6 alkylene group, and n is an integer ranging from 1 to 5.

The substituent linked to the benzoperylene group in Chemical Formula 1 is not limited to a certain ring of the benzoperylene group but may be substituted with hydrogen in all rings of the benzoperylene group.

The arylene group may include at least one selected from the following Group 1.

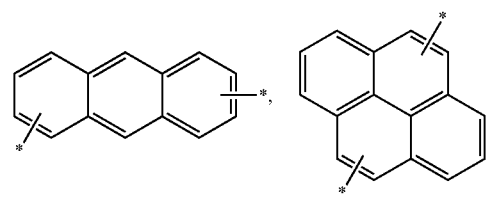

[Group 1]

The monomer for a hardmask composition may be, for example represented by the following Chemical Formula 1a, 1b, or 1c.

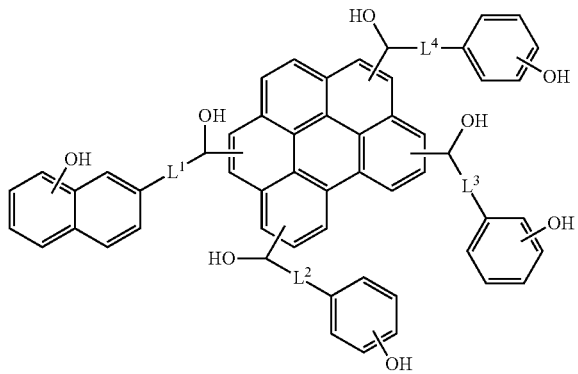

[Chemical Formula 1a]

[Chemical Formula 1b]

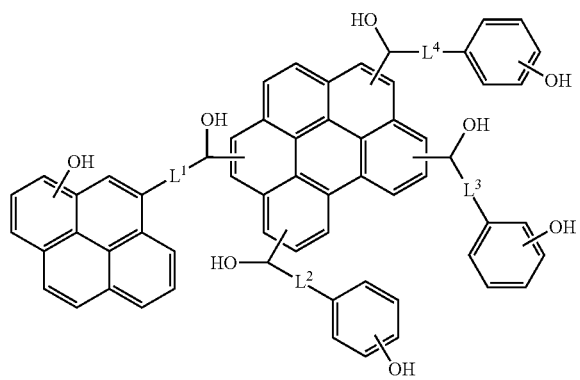

[Chemical Formula 1bb]

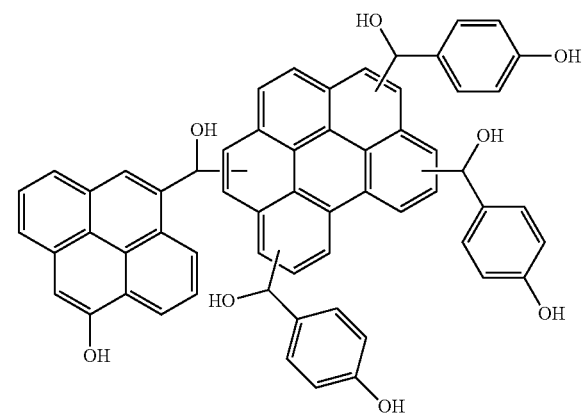

[Chemical Formula 1cc]

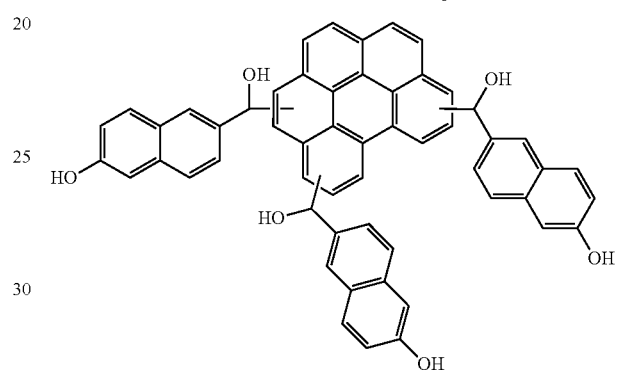

[Chemical Formula 1c]

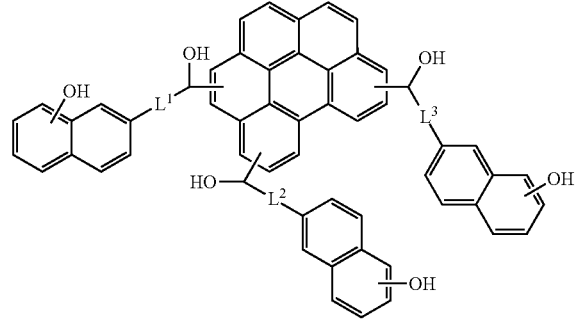

In Chemical Formula 1a, 1b, or 1c, $L^1$ to $L^4$ are each independently a single bond or a substituted or unsubstituted C1 to C6 alkylene group.

The monomer for a hardmask composition may be represented by the following Chemical Formula 1aa, 1bb, or 1cc.

[Chemical Formula 1aa]

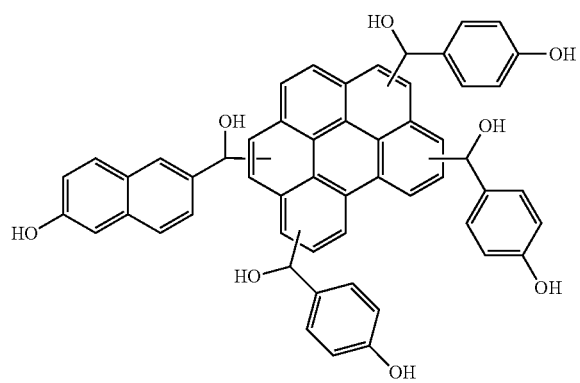

The monomer for a hardmask composition may have a molecular weight about 520 to 1,200.

According to another embodiment, a hardmask composition including the monomer and a solvent is provided.

The monomer may be included in an amount of about 3 to 25 wt % based on the total amount of the hardmask composition.

According to yet another embodiment, provided is a method of forming a pattern that includes providing a material layer on a substrate, applying the hardmask composition on the material layer, heat-treating the hardmask composition to form a hardmask layer, forming a silicon-containing thin layer on the hardmask layer, forming a photoresist layer on the silicon-containing thin layer, exposing and developing the photoresist layer to form a photoresist pattern, selectively removing the silicon-containing thin layer and the hardmask layer using the photoresist pattern to expose a part of the material layer, and etching an exposed part of the material layer.

The hardmask composition may be applied using a spin-on coating method.

The hardmask layer may be heat-treated at about 200 to 500° C.

Advantageous Effect

The hardmask composition satisfies chemical resistance, heat resistance and etch resistance while ensures dissolubility for a solvent, gap-fill characteristics, and planarization characteristics.

BEST MODE

Exemplary embodiments of the present invention will hereinafter be described in detail. However, these embodiments are only exemplary and do not limit the present invention.

As used herein, when a definition is not otherwise provided, the term 'substituted' may refer to a halogen (F, Br, Cl, or I), a hydroxyl group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C4 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, and a combination thereof instead of at least one hydrogen of a compound.

As used herein, when a definition is not otherwise provided, the term "hetero" refers to one including at least one heteroatom selected from N, O, S, and P.

Hereinafter, a monomer for a hardmask composition according to one embodiment is described.

The monomer for a hardmask composition according to one embodiment may be represented by the following Chemical Formula 1.

[Chemical Formula 1]

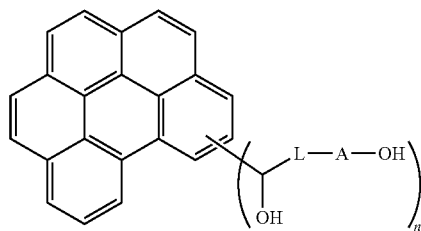

In Chemical Formula 1,

A is a substituted or unsubstituted C6 to C30 arylene group,

L is a single bond or a substituted or unsubstituted C1 to C6 alkylene group, and n is an integer ranging from 1 to 5.

The substituent linked to the benzoperylene group in Chemical Formula 1 is not limited to a certain ring of the benzoperylene group but may be substituted with hydrogen in all rings of the benzoperylene group.

The arylene group may include, for example at least one selected from the following Group 1.

[Group 1]

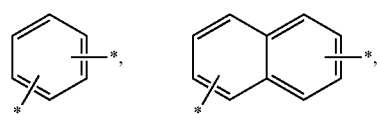

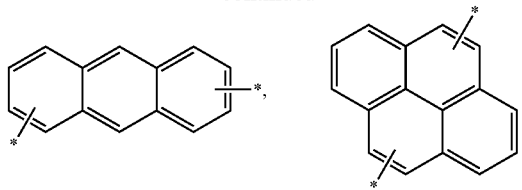

The monomer includes a core of a benzoperylene group and a substituent of a hydroxymethylene group and a hydroxyarylene group as represented by Chemical Formula 1. By the structure, the monomer may have rigid characteristics.

Particularly, the monomer includes a substituent, linked to the benzoperylene group, having a hydroxymethylene group and a hydroxyarylene group, and the two hydroxymethylene group and the hydroxyarylene group may be amplifying cross-linked due to the condensation reaction to provide excellent cross-linking characteristics.

Accordingly, the monomer may be cross-linked as a polymer having a high molecular weight within a short time during the heat treatment to provide excellent characteristics required for the hardmask layer such as excellent mechanical characteristics, heat resistance, chemical resistance, and etch resistance.

In addition, the monomer has a high dissolubility for a solvent by including a plurality of hydroxy groups in the substituent, so as to provide as a solution. Thereby, it may be spin-on coated to provide excellent gap-fill characteristics and planarization characteristics.

The monomer may be represented by, for example, the following Chemical Formula 1a, 1b, or 1c.

[Chemical Formula 1a]

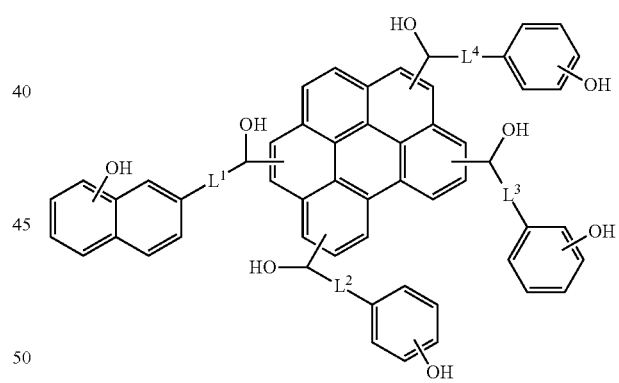

[Chemical Formula 1b]

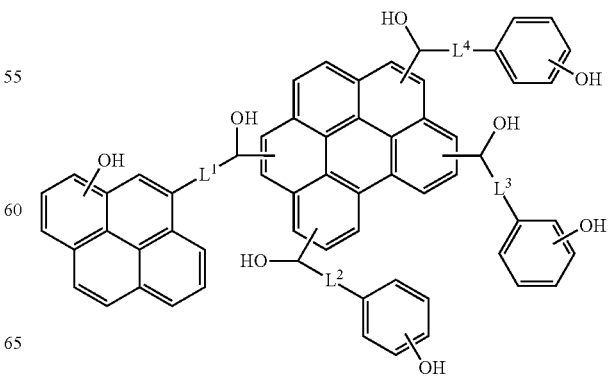

[Chemical Formula 1c]

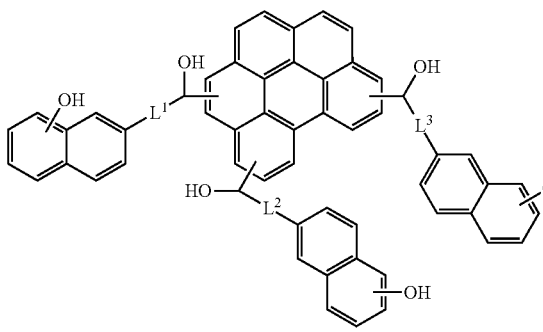

[Chemical Formula 1cc]

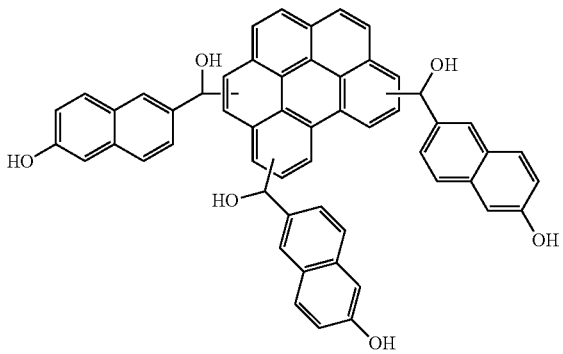

In Chemical Formulae 1a, 1b, or 1c, $L^1$ to $L^4$ are each independently a single bond or a substituted or unsubstituted C1 to C6 alkylene group.

The monomer may be, for example represented by the following Chemical Formula 1aa, 1bb, or 1cc.

[Chemical Formula 1aa]

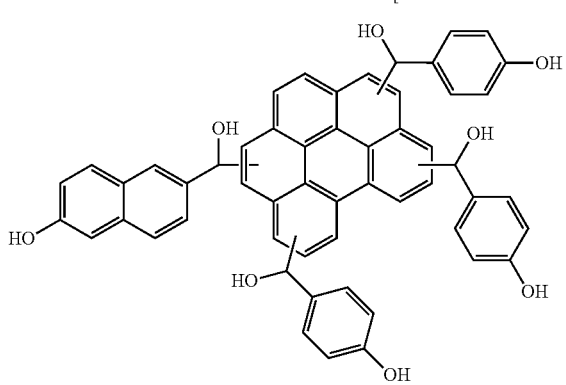

[Chemical Formula 1bb]

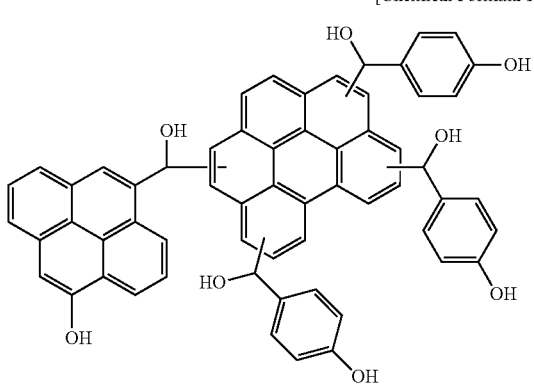

The monomer for a hardmask composition may have a molecular weight about 520 to 1,200. When the monomer has a molecular weight within the above range, a carbon content and solubility for a solvent of a hardmask composition including the monomer may be adjusted to be optimized.

Hereinafter, a hardmask composition according to one embodiment is described.

The hardmask composition according to one embodiment includes the monomer and a solvent.

The monomer is the same as described above, and one kind of monomer may be used singularly and two kinds of monomers may be mixed.

The solvent may be anyone having sufficient dissolubility or dispersion for the monomer and may be, for example at least one selected from propyleneglycol, propyleneglycol diacetate, methoxy propanediol, diethyleneglycol, diethyleneglycol butylether, tri(ethyleneglycol)monomethylether, propyleneglycol monomethylether, propyleneglycol monomethylether acetate, cyclohexanone, ethyllactate, gamma-butyrolactone, methylpyrrolidone, and acetylacetone.

The monomer may be included in an amount of about 3 to 25 wt % based on the total amount of the hardmask composition. When the monomer is included in the above range, a thickness of a hardmask layer, surface roughness, and planarization may be adjusted to be optimized.

The hardmask composition may further include a surfactant.

The surfactant may include, for example, an alkylbenzene sulfonate salt, an alkyl pyridinium salt, polyethylene glycol, or a quaternary ammonium salt, but is not limited thereto.

The surfactant may be included in an amount of about 0.001 to 3 parts by weight based on 100 parts by weight of the hardmask composition. Within the amount range, the solubility and the cross-linking may be secured while not changing the optical properties of the hardmask composition.

Hereafter, a method for forming patterns by using the hardmask composition is described.

A method of forming a pattern according to one embodiment includes providing a material layer on a substrate, applying a hardmask composition including the monomer and a solvent on the material layer, heat-treating the hardmask composition to form a hardmask layer, forming a silicon-containing thin layer on the hardmask layer, forming a photoresist layer on the silicon-containing thin layer, exposing and developing the photoresist layer to form a photoresist pattern, selectively removing the silicon-containing thin layer and the hardmask layer using the photoresist pattern to expose a part of the material layer, and etching an exposed part of the material layer.

The substrate may be, for example, a silicon wafer, a glass substrate, or a polymer substrate.

The material layer is a material to be finally patterned, for example a metal layer such as an aluminum layer and a copper layer, a semiconductor layer such as a silicon layer, or an insulation layer such as a silicon oxide layer and a silicon nitride layer. The material layer may be formed through a method such as a chemical vapor deposition (CVD) process.

The hardmask composition may be applied by spin-on coating in a form of a solution. Herein, the hardmask composition may be applied at a thickness, for example about 100 Å to 10,000 Å.

The heat-treating the hardmask composition may be performed, for example about 200 to 500° C. for about 1 minute to 30 minutes. During heat-treating, the monomer may cause a self cross-linking and/or mutual cross-linking reaction.

The silicon-containing thin layer may be made of, for example silicon nitride or silicon oxide.

A bottom anti-reflective coating (BARC) may be formed on the silicon-containing thin layer.

The exposure of the photoresist layer may be performed using for example ArF, KrF, or EUV. Also, after the exposure, heat-treating may be performed at about 200 to 500° C.

The etching process of the exposed part of the material layer may be performed through a dry etching process using an etching gas, and the etching gas may be, for example $CHF_3$, $CF_4$, $Cl_2$, $BCl_3$, and a mixed gas thereof.

The etched material layer may be formed in a plurality of pattern, and the plurality of pattern may be a metal pattern, a semiconductor pattern, an insulation pattern, and the like, for example diverse pattern of a semiconductor integrated circuit device.

Mode for Invention

Hereinafter, the present invention is illustrated in more detail with reference to examples. However, they are exemplary embodiments of the present invention and are not limiting.

Synthesis of Monomer

Synthesis Example 1

27.6 g (0.1 mol) of benzoperylene and 22.1 g (0.1 mol) of methoxy naphthoyl chloride together with 500 g of chloroform/dichloromethane mixed solution were introduced into 2 L 3-neck flask and agitated using a stirring bar, and reacted with adding 24.5 g (0.1 mol) of trichloroaluminum little by little. The reactant was agitated at a room temperature for 2 hours. After completing the reaction, 52.88 g (0.31 mol) of methoxy benzoyl chloride was added into the reactant and agitated and reacted with adding 85.7 g (0.35 mol) of trichloroaluminum little by little.

After reacting for 5 hours, trichloroaluminum was removed using water to provide a reactant powder. The reactant powder and 60 g (1 mol) of acetic acid and 48.5 g (0.6 mol) of hydrogen bromide were introduced into 500 mL 3-neck flask and reacted at 130° C. After 6 hours, it was precipitated in water to provide powder. The powder was washed for several times and dissolved in tetrahydrofuran (THF) and reacted with adding 18.98 g (0.5 mol) of lithium aluminum hydride little by little. After completing the reaction, the side product was removed using a water/methanol mixture to provide a monomer represented by the following Chemical Formula 1aa.

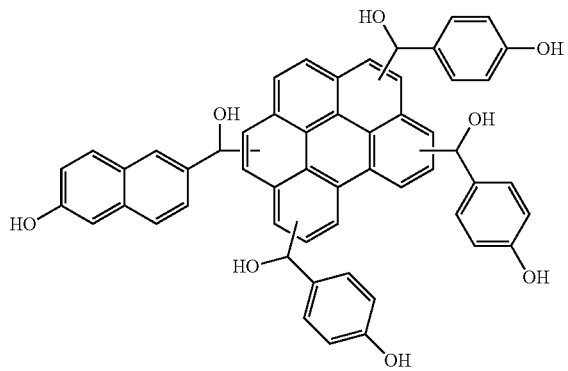

[Chemical Formula 1aa]

Synthesis Example 2

A monomer represented by the following Chemical Formula 1bb was obtained in accordance with the same procedure as Example 1, except that 91.14 g of 0.1 mol methoxy pyrenyl chloride was used instead of 0.1 mol of methoxy naphthoyl chloride.

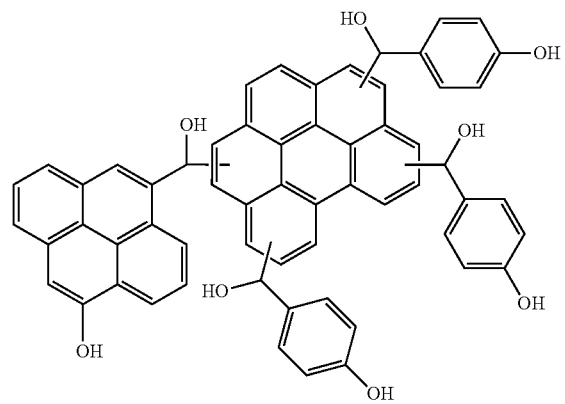

[Chemical Formula 1bb]

Synthesis Example 3

27.6 g (0.1 mol) of benzoperylene and 68.4 g (0.32 mol) of methoxy naphthoyl chloride together with 500 g of chloroform/dichloromethane mixed solution were introduced into 2 L 3-neck flask and agitated using a stirring bar, and reacted with added with 85.7 g (0.35 mol) of trichloroaluminum little by little. After completing the reaction, trichloroaluminum was removed using water to provide a reactant powder. The reactant powder and 60 g (1 mol) of acetic acid and 48.5 g (0.6 mol) of hydrogen bromide were introduced into 500 mL 3-neck flask and reacted at 130° C. for 6 hours. It was precipitated in water to provide powder. The powder was washed for several times and dissolved in tetrahydrofuran (THF) and reacted with adding 18.98 g (0.5 mol) of lithium aluminum hydride little by little. After completing the reaction, the side product was removed using a water/methanol mixture to provide a monomer represented by the following Chemical Formula 1cc.

[Chemical Formula 1cc]

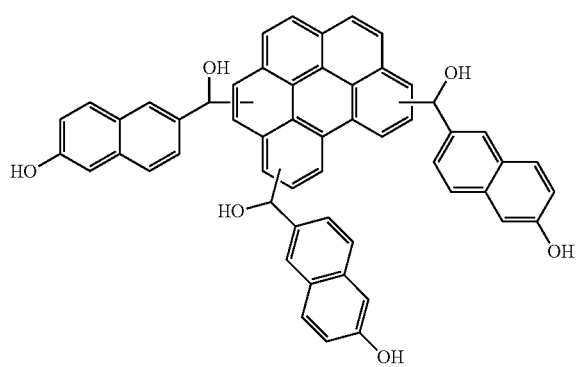

Comparative Synthesis Example 1

A monomer represented by the following Chemical Formula 2 was obtained in accordance with the same procedure as Synthesis Example 3, except that 0.1 mol of pyrenyl chloride was added into the reactor instead of 0.32 mol of methoxy naphthoyl chloride.

[Chemical Formula 2]

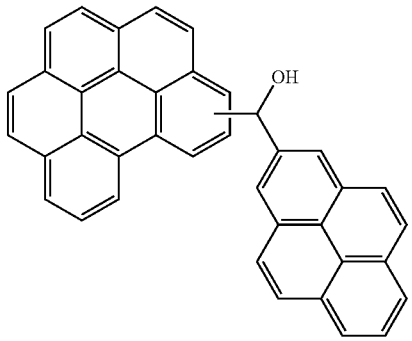

Comparative Synthesis Example 2

A monomer represented by the following Chemical Formula 3 was obtained in accordance with the same procedure as Synthesis Example 3, except that 0.32 mol of naphthoyl chloride was added into the reactor instead of 0.32 mol of methoxy naphthoyl chloride.

[Chemical Formula 3]

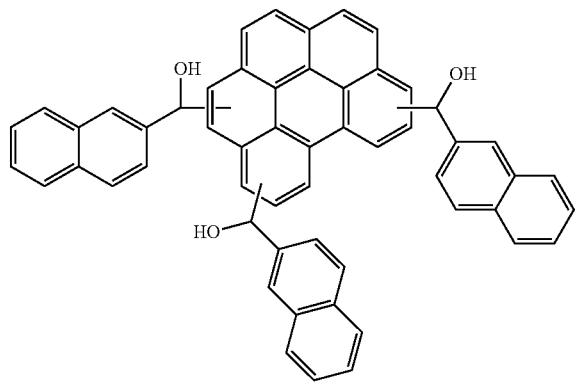

Comparative Synthesis Example 3

500 ml 3-neck flask mounted with a thermometer, a condenser, and a mechanical agitator was prepared, and then the 3-neck flask was immersed into an oil thermostat at 90 to 100° C. While maintaining the constant temperature, it was agitated using a stirring bar. 28.83 g (0.2 mol) of 1-naphthol, 28.32 g (0.14 mol) of pyrene, and 12.0 g (0.34 mol) of paraformaldehyde were introduced into the 3-neck flask, and 0.19 g (1 mmol) of p-toluene sulfonic acid monohydrate was dissolved in 162 g of propylene glycol monomethyl ether acetate (PGMEA) to provide a solution. The solution was introduced into the 3-neck flask and reacted with agitation for 5 to 12 hours.

Every one hour, a sample was taken from the polymerization reactant and measured for a weight average molecular weight. The reaction was completed until reaching the weight average molecular weight to 1,800 to 2,500.

After completing the polymerization, the reactant was slowly cooled to a room temperature, and then the reactant was input into 40 g of distilled water and 400 g of methanol and vigorously agitated and was allowed to stand. The supernatant was removed, and the precipitate was dissolved in 80 g of propylene glycol monomethyl ether acetate (PGMEA), and then it was vigorously agitated using 320 g of methanol and allowed to stand (first step). The obtained supernatant was removed again, and the precipitate was dissolved in 80 g of propylene glycol monomethyl ether acetate (PGMEA) (second step). The first and second steps refer to the first purifying process, and the purifying process was repeated for three times. The purified polymer was dissolved in 80 g of propylene glycol monomethyl ether acetate (PGMEA), and then methanol and distilled water remained in the solution were removed under the reduced pressure to provide a polymer represented by the following Chemical Formula 4.

[Chemical Formula 4]

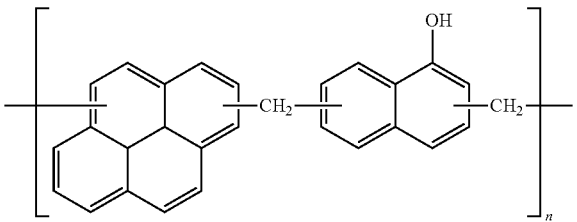

The polymer had a weight average molecular weight of 2,320 and a dispersion of 1.38.

Preparation of Hardmask Composition

Example 1

The monomer obtained from Synthesis Example 1 was dissolved in a mixed solvent (40:20:40 (v/v/v)) of propylene glycol monomethyl ether acetate (PGMEA), methylpyrrolidone, and gamma-butyrolactone and filtered to provide a hardmask composition.

Example 2

A hardmask composition was prepared in accordance with the same procedure as Example 1, except that the monomer obtained from Synthesis Example 2 was used instead of the monomer obtained from Synthesis Example 1.

Example 3

A hardmask composition was prepared in accordance with the same procedure as Example 1, except that the monomer obtained from Synthesis Example 3 was used instead of the monomer obtained from Synthesis Example 1.

Comparative Example 1

A hardmask composition was prepared in accordance with the same procedure as Example 1, except that the monomer obtained from Comparative Synthesis Example 1 was used instead of the monomer obtained from Synthesis Example 1.

Comparative Example 2

A hardmask composition was prepared in accordance with the same procedure as Example 1, except that the monomer obtained from Comparative Synthesis Example 2 was used instead of the monomer obtained from Synthesis Example 1.

Comparative Example 3

A hardmask composition was prepared in accordance with the same procedure as Example 1, except that the monomer obtained from Comparative Synthesis Example 3 was used instead of the monomer obtained from Synthesis Example 1.

Evaluation 1: Optical Properties

Each hardmask composition obtained from Examples 1 to 3 was spin-on coated on a silicon wafer formed with silicon nitride and heat-treated at 400° C. for 120 seconds to provide a hardmask layer having a thickness of 800 Å.

The hardmask layer was measured for a refractive index (n) and extinction coefficient (k). The refractive index and the extinction coefficient were measured using Ellipsometer (manufactured by J. A. Woollam) while irradiating light having a wavelength of 193 nm to 633 nm.

The results are shown in Table 1.

TABLE 1

|  | Optical properties 193 nm | | Optical properties 633 nm | |
| --- | --- | --- | --- | --- |
|  | Refractive index (n) | Extinction coefficient (k) | Refractive index (n) | Extinction coefficient (k) |
| Example 1 | 1.302 | 0.563 | 1.901 | 0.077 |
| Example 2 | 1.298 | 0.648 | 1.899 | 0.127 |
| Example 3 | 1.253 | 0.776 | 1.804 | 0.038 |

Referring to Table 1, it is understood that the hardmask layers formed by the hardmask compositions according to Examples 1 to 3 had a refractive index (n) and an extinction coefficient (k) appropriate to be applied for a hardmask layer and also may be applied for a hardmask layer even in a patterning process using a light source having a low wavelength such as 193 nm.

Evaluation 2: Chemical Resistance

Each hardmask composition obtained from Examples 1 to 3 and Comparative Examples 1 to 3 was spin-on coated on a silicon wafer and then heat-treated on a hot plate at 240° C. for 1 minute to provide a hardmask layer. The hardmask layer was measured for an initial thickness.

Subsequently, the hardmask layer was immersed in a mixed solvent (7:3 (v/v)) of ethyl 3-ethoxypropinonate (EEP) and ethyl lactate (EL) as a stripping solution for 1 minute and taken out. The thickness of hardmask layer was measured again.

The hardmask layer was observed for the thickness change and the stain appearance.

The thickness change was measured by a thin layer thickness gauge manufactured by K-MAC, and the stain appearance was monitored by naked eyes.

The results are shown in Table 2.

TABLE 2

|  | Changes of thickness (ΔT) | | |
| --- | --- | --- | --- |
|  | Decreased thickness (Å) | Thickness decrease ratio (%) | Stain |
| Example 1 | 24 | 0.17 | X |
| Example 2 | 60 | 0.06 | X |
| Example 3 | 76 | 0.08 | X |
| Comparative Example 1 | 319 | 34 | O |
| Comparative Example 2 | 230 | 22 | O |
| Comparative Example 3 | 132 | 14 | O |

Referring to Table 2, the hardmask layers formed by hardmask compositions according to Examples 1 to 3 had less thickness decrease ratio and no stain after immersing in the stripping solution compared to the hardmask layers formed by hardmask compositions according to Comparative Examples 1 to 3.

From the results, it is confirmed that the hardmask compositions according to Examples 1 to 3 were sufficiently cross-linked by the heat-treatment at the relatively low temperature of 240° C. to provide a thin layer having high chemical resistance compared to the hardmask compositions according to Comparative Examples 1 to 3.

Evaluation 3: Film Density

Each hardmask composition according to Examples 1 to 3 was spin-coated on a silicon wafer and then heat-treated on a hot plate at 240° C. for one minute to provide a hardmask layer having a thickness of 300 Å.

In addition, each hardmask composition according to Examples 1 to 3 was spin-on coated on a silicon wafer and then heat-treated on a hot plate at 400° C. for one minute to provide a hardmask layer having a thickness of 300 Å.

The hardmask layer was measured for a film density using a X-ray Diffractometer (Model: X'pert PRO MPD, manufactured by Panalytical (Netherlands)).

The results are shown in Table 3.

TABLE 3

|  | Film density (g/cm³) | |
| --- | --- | --- |
|  | 240° C. | 400° C. |
| Example 1 | 1.35 | 1.39 |
| Example 2 | 1.37 | 1.40 |
| Example 3 | 1.35 | 1.41 |

Referring to Table 3, it is understood that the hardmask layers using the hardmask compositions according to Example 1 to 3 had a sufficient film density of greater than or equal to 1, the film density is higher as increasing the heat treatment temperature. From the results, since the hardmask compositions according to Examples 1 to 3 had high cross-linking degree, it is understood that the layer formed therefrom had a sufficient film density. It is understood that the hardmask layer heated at a high temperature (400° C.) may form a layer having denser structure to prevent the permeation of pollution material that may be eluted from a substrate or a lower layer.

Evaluation 4: Formation of Pattern

Each hardmask composition according to Examples 1 to 3 and Comparative Examples 1 to 3 was coated on a silicon wafer by a spin-on coating method and heat treated on a hot plate at 400° C. for 2 minutes to provide a hardmask layer. Subsequently, a silicon nitride (SiN) layer was formed in a thickness of 300 Å according to the chemical vapor deposition, and a KrF photoresist was coated thereon and heat-treated at 110° C. for 60 seconds and exposed using ASML (XT: 1400, NA 0.93) exposure equipment and developed with tetramethylammonium hydroxide (2.38 wt % of TMAH aqueous solution). The silicon nitride layer was dry-etched using a $CHF_3/CF_4$ mixed gas, and the hardmask layer was dry-etched using a $Cl_2/HBr/O_2/N_2$ mixed gas. After patterning by the dry etching, the thickness of thin layer was measured and the pattern shape was observed.

The bulk etch rate (BER) was obtained by dry etching the coated hardmask layer without patterning and dividing the thin layer thickness difference of between the initial thin layer thickness and the thin layer thickness after the etched by the etched time (second). The pattern shape was confirmed by observing the cross-sectional surface of hardmask pattern using a scanning electron microscope (SEM) after patterned, and the pattern forming result was confirmed by the width ratio of top and bottom. As approaching the top/bottom ratio to 1, it means to be isotropic patterned in a vertical.

The results are shown in Table 4.

TABLE 4

|  | Bulk etch rate (Å/s) | Top/bottom ratio of pattern |
|---|---|---|
| Example 1 | 23.7 | 0.80 |
| Example 2 | 23.5 | 0.78 |
| Example 3 | 22.7 | 0.84 |
| Comparative Example 1 | 23.1 | 0.66 |
| Comparative Example 2 | 24.0 | 0.71 |
| Comparative Example 3 | 25.3 | 0.63 |

Referring to Table 4, the hardmask layers formed using the hardmask compositions according to Examples 1 to 3 had sufficient etch resistance to the etching gas compared to the hardmask layers formed using the hardmask compositions according to Comparative Examples 1 to 3, so it is understood that it was isotropic patterned near to the vertical.

Evaluation 5: Planarization and Gap-Fill Characteristics

Each hardmask composition according Examples 1 to 3 and Comparative Examples 1 to 3 was spin-coated on the patterned silicon wafer at 1,200 rpm and 2,500 rpm and heat-treated at 400° C., and then the gap-fill characteristics and the planarization characteristics were observed using a V-SEM equipment.

The gap-fill characteristics were determined by observing the cross sectional surface of pattern using a scanning electron microscope (SEM) and counting void, and the planarization characteristics were calculated according to the following Equation 1 after measuring the thickness of hardmask layer from the image of pattern cross-sectional surface observed from SEM. The planarization characteristics are more excellent as smaller the difference between $h_1$ and $h_2$, so the planarization characteristics are better as smaller the number.

[Equation 1]

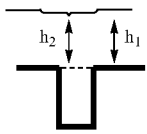

$$\text{Planarization} = \left(1 - \frac{h_2}{h_1}\right) \times 100$$

The results are shown in Table 5.

TABLE 5

|  | Planarization characteristic | | Gap-fill |
|---|---|---|---|
|  | 1,200 rpm | 2,500 rpm | characteristic |
| Example 1 | 13.51 | 28.95 | No void |
| Example 2 | 15.45 | 23.67 | No void |
| Example 3 | 12.27 | 27.13 | No void |
| Comparative Example 1 | 18.86 | 65.36 | No void |
| Comparative Example 2 | 17.05 | 60.73 | No void |
| Comparative Example 3 | 21.12 | 68.28 | No void |

Referring to Table 5, the case of using the hardmask compositions according to Examples 1 to 3 had better planarization and no void than the case of using hardmask compositions according to Comparative Examples 1 to 3, so it is understood that had excellent gap-fill characteristics. Particularly, when spin-on coated at a high rate of 2,500 rpm, the case of using hardmask compositions according to Examples 1 to 3 had improved the planarization characteristics at greater than or equal to 2 times compared to the case of using the hardmask compositions according to Comparative Examples 1 to 3.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A monomer for a hardmask composition represented by the following Chemical Formula 1:

[Chemical Formula 1]

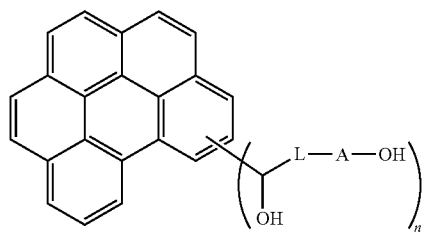

wherein, in Chemical Formula 1,

A is a substituted or unsubstituted C6 to C30 arylene group,

L is a single bond or a substituted or unsubstituted C1 to C6 alkylene group, and n is an integer ranging from 1 to 5.

2. The monomer for a hardmask composition of claim 1, wherein the arylene group comprises at least one selected from the following Group 1:

[Group 1]

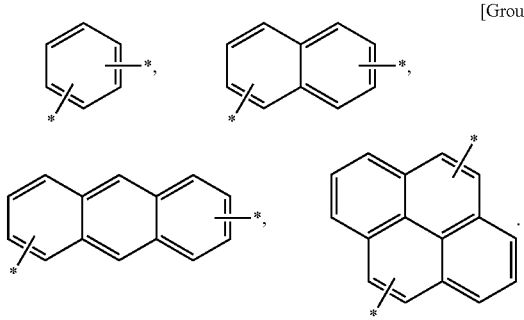

3. The monomer for a hardmask composition of claim 1, wherein the monomer is represented by the following Chemical Formula 1a, 1b, or 1c:

[Chemical Formula 1a]

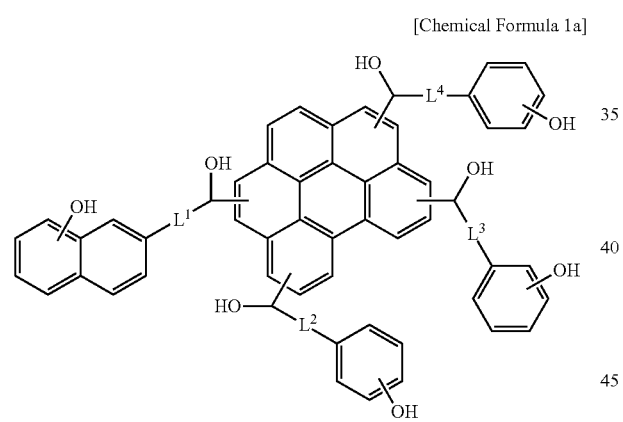

[Chemical Formula 1b]

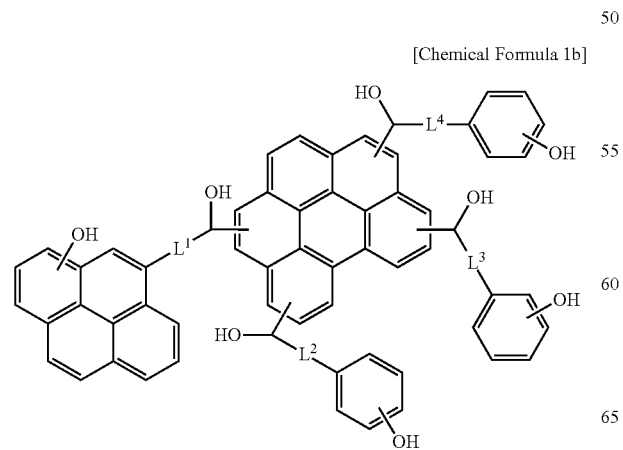

[Chemical Formula 1c]

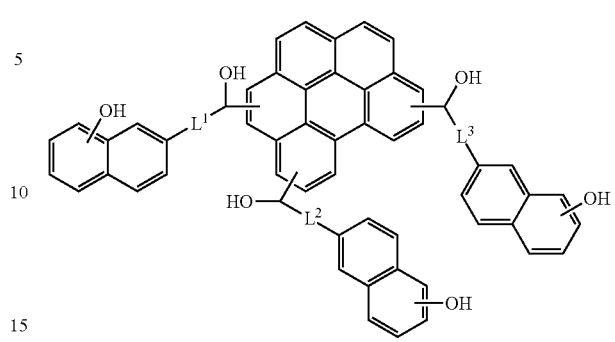

wherein, in Chemical Formula 1a, 1b, or 1c, $L^1$ to $L^4$ are each independently a single bond or a substituted or unsubstituted C1 to C6 alkylene group.

4. The monomer for a hardmask composition of claim 3, wherein the monomer is represented by the following Chemical Formula 1aa, 1bb or 1cc:

[Chemical Formula 1aa]

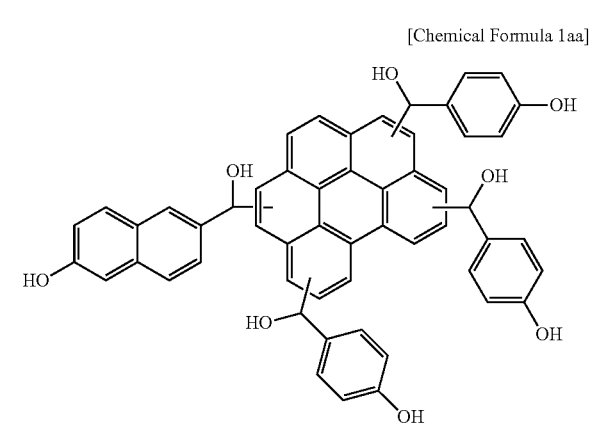

[Chemical Formula 1bb]

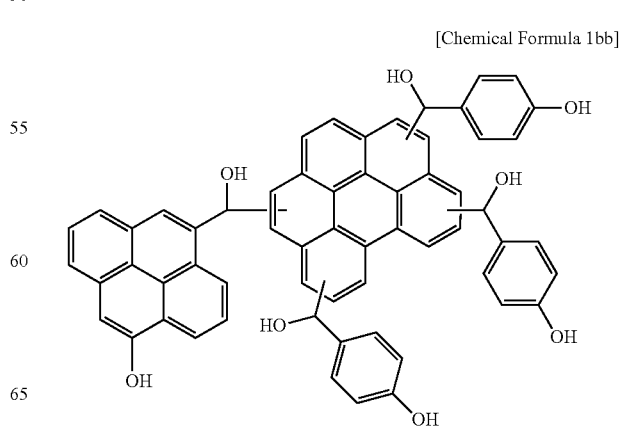

-continued

[Chemical Formula 1cc]

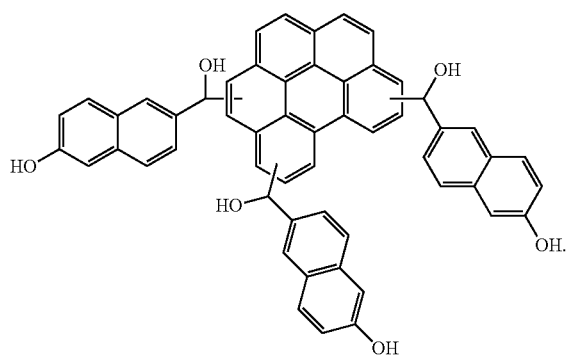

5. The monomer for a hardmask composition of claim 1, wherein the monomer has a molecular weight of about 520 to 1,200.

6. A hardmask composition, comprising
the monomer of claim 1, and
a solvent.

7. The hardmask composition of claim 6, wherein the monomer is included in an amount of about 3 to 25 wt % based on the total amount of the hardmask composition.

8. A method of forming a pattern, comprising
providing a material layer on a substrate,
applying the hardmask composition according to claim 6 on the material layer,
heat-treating the hardmask composition to form a hardmask layer,
forming a silicon-containing thin layer on the hardmask layer,
forming a photoresist layer on the silicon-containing thin layer,
exposing and developing the photoresist layer to form a photoresist pattern
selectively removing the silicon-containing thin layer and the hardmask layer using the photoresist pattern to expose a part of the material layer, and
etching an exposed part of the material layer.

9. The method of claim 8, wherein the hardmask composition is applied using a spin-on coating method.

10. The method of claim 8, wherein, in the heat-treating of the hardmask composition to form the hardmask layer, the hardmask composition layer is heat-treated at about 200 to 500° C.

* * * * *